(12) United States Patent
Boutillette (10) Patent No.: US 8,556,857 B2
(45) Date of Patent: *Oct. 15, 2013

(54) CATHETER INCORPORATING A GUIDEWIRE EXIT RAMP

(75) Inventor: Michael P. Boutillette, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/545,757

(22) Filed: Jul. 10, 2012

(65) Prior Publication Data

US 2012/0277731 A1    Nov. 1, 2012

Related U.S. Application Data (63) Continuation of application No. 12/939,899, filed on Nov. 4, 2010, now Pat. No. 8,221,357, which is a continuation of application No. 11/543,320, filed on Oct. 5, 2006, now Pat. No. 7,833,197, which is a continuation of application No. 10/917,974, filed on Aug. 12, 2004, now abandoned.

(51) Int. Cl.
*A61M 5/178* (2006.01)

(52) U.S. Cl.
USPC ............... 604/160; 604/164.13; 604/528

(58) Field of Classification Search
USPC ............ 604/160, 161, 528, 164.01, 164.13
See application file for complete search history.

(56) References Cited

U.S. PATENT DOCUMENTS

| | | |
|---|---|---|
| 1,719,428 A | 7/1929 | Friedman |
| 4,932,413 A | 6/1990 | Shockey et al. |
| 4,947,864 A | 8/1990 | Shockey et al. |
| 5,030,210 A | 7/1991 | Alchas |
| 5,091,205 A | 2/1992 | Fan |
| 5,135,535 A | 8/1992 | Kramer |
| 5,156,594 A | 10/1992 | Keith |
| 5,281,203 A | 1/1994 | Ressemann |
| 5,306,247 A | 4/1994 | Pfenninger |
| 5,342,301 A | 8/1994 | Saab |
| 5,360,330 A | 11/1994 | Jensen et al. |
| 5,387,226 A | 2/1995 | Miraki |

(Continued)

FOREIGN PATENT DOCUMENTS

| | | |
|---|---|---|
| WO | WO 95/02430 | 1/1995 |
| WO | WO 99/44667 | 9/1999 |
| WO | WO 00/69500 | 11/2000 |
| WO | WO 2006/020374 | 2/2006 |

*Primary Examiner* — Theodore Stigell (74) *Attorney, Agent, or Firm* — Seager, Tufte & Wickhem LLP (57) ABSTRACT

Guidewire exit ramp members that may be placed over a tubular member having a guidewire lumen, which longitudinally extending and laterally accessible, and methods of use. The guidewire exit ramp member can be placed to force a guidewire loaded through the lumen in a first direction to be forced out of the lumen via an opening, slit or channel. The guidewire exit ramp member, in an illustrative embodiment, takes the form of a relatively short member having a proximal portion and a distally extending flap. The flap may be designed to enter and remain in a longitudinally accessible guidewire lumen. Combinations of such ramp members and device shafts having longitudinally extending laterally accessible guidewire lumens are also disclosed, as are methods for securing such combinations together. A method of backloading a guidewire into a catheter while causing lateral exit of the guidewire at a desired location is also shown.

19 Claims, 9 Drawing Sheets

(56) References Cited

U.S. PATENT DOCUMENTS

| | | |
|---|---|---|
| 5,389,087 A | 2/1995 | Miraki |
| 5,415,639 A | 5/1995 | VandenEinde et al. |
| 5,449,362 A | 9/1995 | Chaisson et al. |
| 5,501,667 A | 3/1996 | Verduin, Jr. |
| 5,540,236 A | 7/1996 | Ginn |
| 5,645,533 A | 7/1997 | Blaeser et al. |
| 5,690,613 A | 11/1997 | Verbeek |
| 5,690,644 A | 11/1997 | Yurek et al. |
| 5,709,658 A | 1/1998 | Sirhan et al. |
| 5,738,667 A | 4/1998 | Solar |
| 5,807,355 A | 9/1998 | Ramzipoor et al. |
| 5,817,053 A | 10/1998 | Agarwal |
| 5,824,173 A | 10/1998 | Fontirroche et al. |
| 5,843,050 A | 12/1998 | Jones et al. |
| 5,876,375 A | 3/1999 | Penny |
| 5,919,175 A | 7/1999 | Sirhan |
| 5,921,971 A | 7/1999 | Agro et al. |
| 5,947,927 A | 9/1999 | Mertens |
| 5,980,486 A | 11/1999 | Enger |
| 5,984,945 A | 11/1999 | Sirhan |
| 6,030,369 A | 2/2000 | Engelson et al. |
| 6,106,487 A | 8/2000 | Duane et al. |
| 6,129,708 A | 10/2000 | Enger |
| 6,143,013 A | 11/2000 | Samson et al. |
| 6,190,358 B1 | 2/2001 | Fitzmaurice et al. |
| 6,193,685 B1 | 2/2001 | Goodin |
| 6,248,092 B1 | 6/2001 | Miraki et al. |
| 6,254,549 B1 | 7/2001 | Ramzipoor |
| 6,319,229 B1 | 11/2001 | Kim et al. |
| 6,344,029 B1 | 2/2002 | Estrada et al. |
| 6,346,093 B1 | 2/2002 | Allman et al. |
| 6,361,529 B1 | 3/2002 | Goodin et al. |
| 6,368,302 B1 | 4/2002 | Fitzmaurice et al. |
| 6,398,799 B2 | 6/2002 | Kramer |
| 6,409,863 B1 | 6/2002 | Williams et al. |
| 6,475,187 B1 * | 11/2002 | Gerberding ............... 604/102.02 |
| 6,503,223 B1 | 1/2003 | Sekido et al. |
| 6,514,217 B1 * | 2/2003 | Selmon et al. ................. 600/585 |
| 6,520,951 B1 | 2/2003 | Carrillo, Jr. et al. |
| 6,524,285 B1 | 2/2003 | Sirhan |
| 6,554,795 B2 | 4/2003 | Bagaoisan et al. |
| 6,605,062 B1 | 8/2003 | Hurley et al. |
| 6,606,515 B1 | 8/2003 | Windheuser et al. |
| 6,723,071 B2 * | 4/2004 | Gerdts et al. ............. 604/103.04 |
| 6,997,938 B2 | 2/2006 | Wang et al. |
| 7,833,197 B2 * | 11/2010 | Boutillette .................... 604/160 |
| 2005/0049552 A1 | 3/2005 | Holzapfel et al. |

* cited by examiner

CATHETER INCORPORATING A GUIDEWIRE EXIT RAMP

RELATED APPLICATIONS

This application is a continuation of U.S. application Ser. No. 12/939,899, filed Nov. 4, 2010, now U.S. Pat. No. 8,221,357; which is a continuation of U.S. application Ser. No. 11/543,320, filed Oct. 5, 2006, now U.S. Pat. No. 7,833,197; which is a continuation of U.S. application Ser. No. 10/917,974, filed Aug. 12, 2004, abandoned, the entire disclosures of which are incorporated herein by reference.

FIELD

The present invention is related to the field of medical devices. More particularly, the present invention is related to catheters and other elongate medical devices incorporating guidewire lumens.

BACKGROUND

The use of catheters for minimally invasive medical procedures has become widespread. In many such procedures, a guidewire is used to help place the distal end of a catheter at a desired location. In practice, the use of a guidewire and an elongate medical device such as a catheter can create a number of difficulties.

If a guidewire or catheter proves unsuitable once inserted into a patient, it is removed and replaced. With early technologies, the catheter typically tracked over the guidewire along its entire length. When a catheter was removed, these early technologies required allowing the entire length of the catheter (typically 150 cm or longer) to pass over the guidewire without releasing the proximal end of the guidewire. This required a guidewire having a length of at least 300 cm, or a shorter guidewire used in combination with a guidewire extension. Such long guidewires required extra hands in the operating arena, increasing costs and creating a greater risk of loss of sterility, as well as making procedures last longer.

Rapid exchange catheters and single operator exchange catheters have been developed to make it easier and quicker to substitute one catheter or guidewire for another. An example single operator exchange catheter is the Autotome™ RX sphincterotome, marketed by Boston Scientific Corporation, Natick, Mass., which makes use of an elongated guidewire lumen in the form of a C-shaped channel.

The C-shaped channel allows lateral movement of a guidewire out of the guidewire lumen through the opening in the C-shaped channel over the longitudinal length of the channel. Such an opening, as well as openings or accesses created by the use of C-shaped, U-shaped, perforated or slit guidewire lumens, makes the longitudinally extending guidewire lumen a laterally accessible guidewire lumen. Lumens having a weakened, thin, or thinned wall through which a guidewire may tear for removal may also be considered as including a laterally accessible guidewire lumen.

SUMMARY

The present invention, in an illustrative embodiment, includes a guidewire exit ramp member that may be placed over a tubular member having a longitudinally extending guidewire lumen that is laterally accessible generally continuously over at least a portion of the length of the tubular member. The guidewire exit ramp member can be placed to force a guidewire passing into the guidewire lumen in a first direction to be forced out of the lumen via an opening, slit or channel. The guidewire exit ramp member, in an illustrative embodiment, takes the form of a ramp member having a proximal portion and a distally extending flap. The flap may be designed to enter and remain in a longitudinally extending laterally accessible guidewire lumen.

Another illustrative embodiment includes a method of providing a guidewire exit location for an elongate medical device. A guidewire exit ramp member is placed on an elongate member having a longitudinally extending guidewire lumen with a slit or opening therein over a certain length. The elongate member may include a skive or other opening into the guidewire lumen. The guidewire exit ramp member is placed near the skived portion or opening and slid in a direction such that a flap of the guidewire exit ramp member goes through the skive into the guidewire lumen. In some embodiments, the guidewire exit ramp member may be secured in place by heat bonding, adhesive, or the other attachment methods. When the method is complete, a guidewire passed through the guidewire lumen in a first direction is forced out of the guidewire lumen by the flap of the guidewire exit ramp member. In a further embodiment, the flap is flexible enough such that, when a guidewire is passed through the guidewire lumen in a second direction, the guidewire readily passes by the flap with little or no added resistance.

DETAILED DESCRIPTION

The following detailed description should be read with reference to the drawings. The drawings, which are not necessarily to scale, depict illustrative embodiments and are not intended to limit the scope of the invention.

Figure 1A:
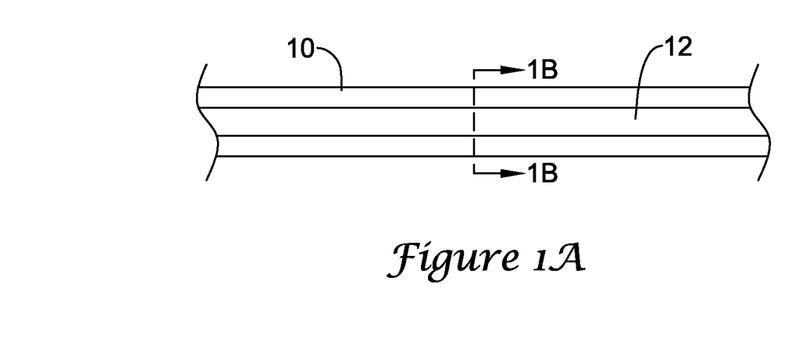
FIG. 1A is a partial elevational view of a medical device shaft having a longitudinally extending laterally accessible guidewire lumen.
Figure 1B:
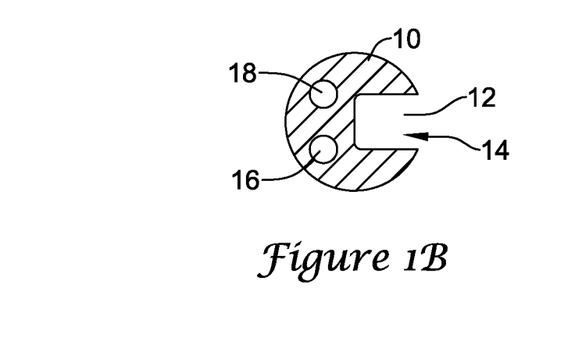
FIG. 1B is a cross-sectional view along line 1B-1B of FIG. 1A.

FIG. 1A is a partial elevational view of a medical device shaft having a longitudinally extending laterally accessible guidewire lumen. The shaft 10 includes a channel 12 for laterally accessing a guidewire lumen passing therethrough. FIG. 1B is a cross-sectional view along line 1B-1B of FIG. 1A. As illustrated by FIG. 1B, the guidewire lumen 14 includes the channel 12. Two auxiliary lumens 16, 18 are also illustrated. While a triple lumen shaft 10 is illustrated, any number of lumens, from a single lumen up to 3, 4, or more lumens, may be provided in a shaft for use with the present invention.

The channel 12 is illustrated for providing access to a generally U-shaped guidewire lumen. Instead of a U-shape, a C-shape may be provided, the C-shape helping to retain a guidewire in the lumen 14. Additionally, a slit may be used. Alternatively, instead of a channel 12 creating an opening, a wall for the lumen 14 where the channel is shown may be thin or intentionally thinned to enable a guidewire to be torn therethrough. Perforations may also be provided to make the longitudinally extending guidewire lumen 14 laterally accessible. Laterally accessible, as used herein, refers to a guidewire lumen that can be accessed along a length thereof, where access can be had either through an existing opening or by tearing a guidewire disposed in the guidewire lumen laterally through a slit, thin, thinned, perforated, or otherwise relatively weak lumen wall section.

Figure 2:
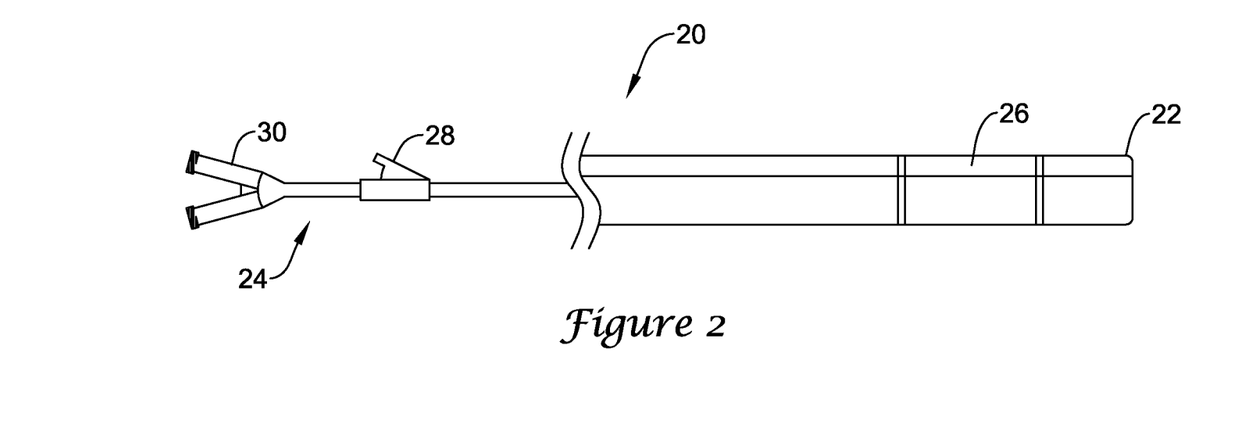
FIG. 2 is a plan view of a cannula including a longitudinally extending laterally accessible guidewire lumen.

FIG. 2 is a plan view of a cannula including a longitudinally extending laterally accessible guidewire lumen. The cannula 20 may incorporate a shaft 10 as illustrated in FIGS. 1A and 1B having a distal end 22 and a proximal end 24. A slit 26 extends along a length of the shaft toward the distal end 22; while not shown, the slit 26 may extend proximally to a guidewire entry adaptor 28. The example also illustrates marker bands near the distal end. Proximal of the adaptor 28 is a manifold 30 including two fluid infusion ports. The cannula in FIG. 2 may have a similar cross section to that shown in FIG. 1B, except to the extent that a slit 26 is used instead of an opening. The fluid infusion ports on the manifold 30 may be coupled to the auxiliary lumens of the cannula shaft for infusing fluids to a location at or near the distal end 22.

The adaptor 28 shown functions by having a side-directed ramp/lumen with an opening allowing for lateral removal of a guidewire therefrom. The proximal end of the guidewire is controlled proximal of the adaptor 28 such that there is no need to force a backloaded guidewire from the guidewire lumen. The guidewire can be removed through the slit 26 once the exchange procedure starts. However, the exact location where the guidewire exits the slit 26 is not controlled. In particular, if a guidewire is backloaded into such a rapid exchange catheter, the adaptor 28 does not force the guidewire out of the catheter.

An example and description of such an adaptor 28 is given by Windheuser et al., in U.S. Pat. No. 6,606,515, the disclosure of which is incorporated herein by reference. The adaptor 28 has a relatively large profile in order to achieve ease of guidewire entry through a funnel-shaped portion, as further discussed by Windheuser et al., and is designed to prevent passage of the entire adaptor through a side port in an endoscope. Such sizing would also typically prevent passage through a guide catheter used in a vascular procedure.

During a catheter exchange procedure, with the guidewire already in place at a desired location in the patient (i.e., a vascular location, a location in the biliary tract, or any other cannulated location), the guidewire will extend through the guidewire lumen from the adaptor 28 to the distal end 22. To exchange the cannula 20, the guidewire is moved laterally out of the adaptor 28 and held in place as the cannula 20 is withdrawn. As the cannula 20 is withdrawn, the guidewire passes through the slit 26, remaining in its internal location in the patient without requiring a guidewire extension. The slit 26 may extend to the distal end 22, or may stop proximal of the distal end.

Figure 3:
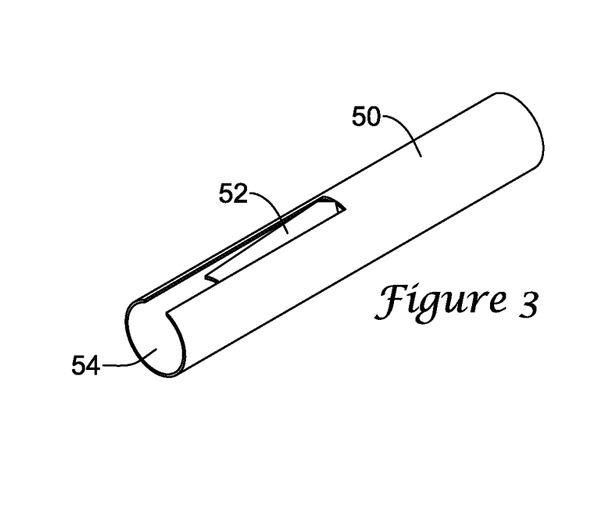
FIG. 3 is a perspective view of a guidewire exit ramp member for use in conjunction with a medical device shaft having a longitudinally extending laterally accessible guidewire lumen.

FIG. 3 is a perspective view of a guidewire exit ramp member for use in conjunction with a medical device shaft having a longitudinally extending laterally accessible guidewire lumen. The illustrative example guidewire exit ramp member includes a proximal portion 50, a proximal end 53, a flap 52, a distal portion 54, and a distal end 55. The distal portion 54 of the guidewire exit ramp may further include a slot 51 defined therein. The proximal portion 50 surrounds and/or tracks over an elongate medical device on which the guidewire exit ramp member is used. The shape is shown as cylindrical but may instead be oval, polygonal, or other shapes including polygons with one or more curved sides.

In other illustrative examples, the proximal portion 50 may only partly surround an elongate medical device, and may instead take the form of a partial cylinder, or may have one or more gaps. In several embodiments, the form illustrated in FIG. 3 is used for its low profile, allowing the guidewire exit ramp member to be readily placed and used even in situations where low profile is a concern.

Figure 4:
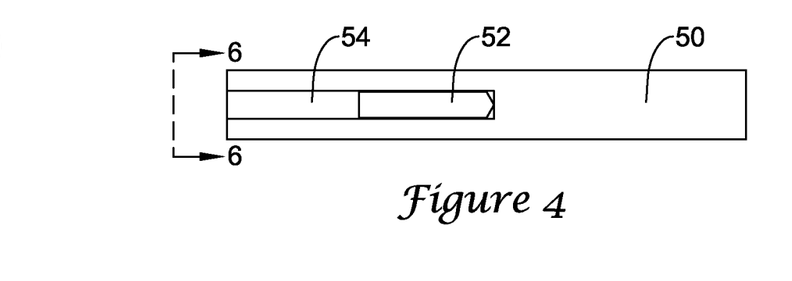
FIG. 4 is an elevation view of the illustrative guidewire exit ramp member of FIG. 3 showing the flap.

FIG. 4 is an elevation view of the illustrative guidewire exit ramp member of FIG. 3 showing the flap 52 more clearly. The flap 52 may have a proximal end 57 connected to the proximal portion 50 of the guidewire ramp member and extending distally therefrom to a distal end 59. In some instances, the distal end 59 of the flap may be flat. As can be seen, the example flap 52 has rather angular distal ends, extending distally relative to, but shorter than, the distal portion 54. In other embodiments the flap 52 may be longer than the distal portion 54, and, in one embodiment, the distal portion 54 may be entirely omitted. For some embodiments, the flap 52 will be inserted through a transversely cut opening in an elongate medical device, as further explained below. For such embodiments, the inclusion of the distal portion 54 may help maintain the shape, pushability, and/or anti-kinking characteristics of the elongate medical device across the transverse cut since the transverse cut may weaken the elongate medical device.

Figure 5:
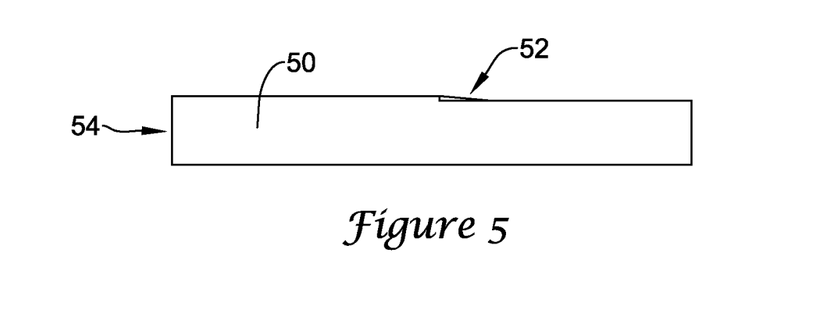
FIG. 5 is a side view of the illustrative guidewire exit ramp member of FIG. 3.
Figure 6:
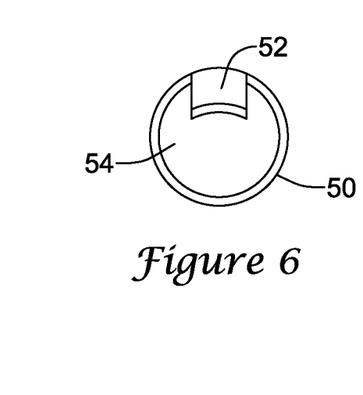
FIG. 6 is an end view from a distal location of the illustrative guidewire exit ramp member of FIG. 3.

FIG. 5 is a side view of the illustrative guidewire exit ramp member of FIG. 3. The distal portion 54 has a reduced profile due to the flap 52. FIG. 6 is an end view of the illustrative guidewire exit ramp member of FIG. 3. The flap 52 is shown extending down into the lumen defined by the distal portion 54, which is in line with the lumen formed in the proximal portion 50. In an illustrative embodiment, the flap 52 is biased to bend down as illustrated by FIGS. 3 and 5-6.

In one embodiment, the guidewire exit ramp member shown in FIGS. 3-6 is formed by a molding process. In other embodiments, the guidewire exit ramp member may be formed by cutting a tubular member. The ramp member may be sized to correspond to a given size of elongate medical device shaft. For example, given a 6-French elongate medical device shaft, the inner diameter defined by the proximal portion of the ramp member may be just large enough to slide over such a device shaft. The inner surface of the ramp member may include a lubricious coating to allow easy movement and placement over the device shaft. Alternatively, the material chosen for making the ramp member may be chosen for its lubricious properties.

The ramp member may be formed of a wide variety of materials. In some embodiments the ramp member is formed of a nylon material, which is inexpensive and easy to mold, as well as being a popular material for medical applications. Polycarbonate may also be used, as well as any of a wide variety of polymers, copolymers and metals or alloys known for use in medical devices, catheters, cannulas, endoscopes, and the like. Any other suitable biocompatible material may also be used and/or incorporated.

Figure 7:
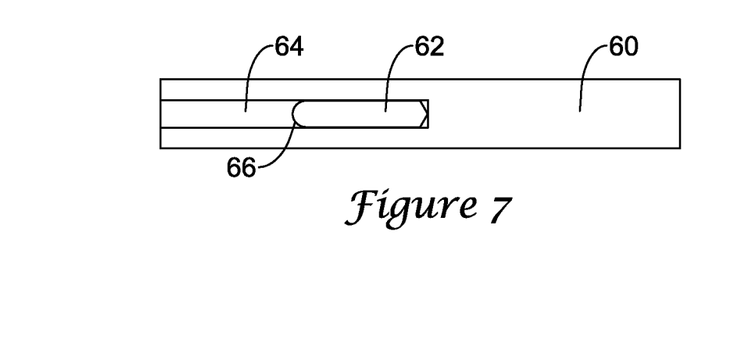
FIG. 7 is an elevation view of an alternative example guidewire exit ramp with a curved flap.

FIG. 7 is an elevation view of an alternative example guidewire exit ramp member with a curved flap. As illustrated, the guidewire exit ramp member includes a proximal portion 60, a proximal end 63, a flap 62, a (optional) distal portion 64, and a distal end 65. The distal portion 64 of the guidewire exit ramp may further include a slot 61 defined therein. As shown at 66, the flap 62 has curved ends, which may allow the flap 62 to extend into and generally match the contours of a guidewire lumen having curved interior contours. Rather than a simple curve as shown, the flap 62 may be designed to match a particular guidewire lumen shape/cross section.

Figure 8A:
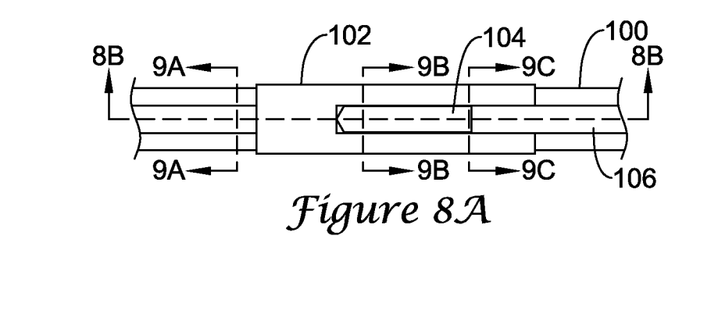
FIG. 8A is an elevation view of an illustrative guidewire exit ramp coupled with a medical device shaft having a longitudinally extending laterally accessible guidewire lumen.
Figure 8B:
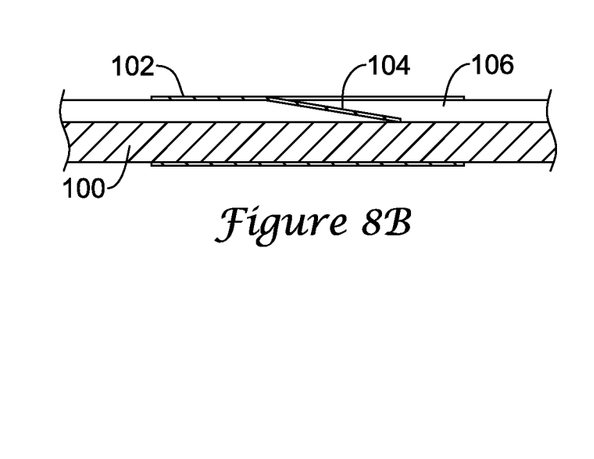
FIG. 8B is a section view along line 8B-8B of FIG. 8A.

FIG. 8A is an elevation view of an illustrative guidewire exit ramp coupled with a medical device shaft having a longitudinally extending laterally accessible guidewire lumen. A device shaft 100 is shown with a guidewire exit ramp member 102 placed thereover. The ramp member 102 may include a proximal end 103 and a distal end 105. The ramp member 102 may further include a slot 101 extending proximally from the distal end 105 The ramp member 102 includes a flap 104 having a proximal end 107 and a distal end 109. The flap 104 is aligned with and enters a channel 106 (shown as a U-shaped channel for the purposes of illustration). The longitudinal cross section of FIG. 8B illustrates that the ramp member 102 has a proximal portion that surrounds the device shaft 100, with the flap 104 extending down into the channel 106.

Figure 9A:
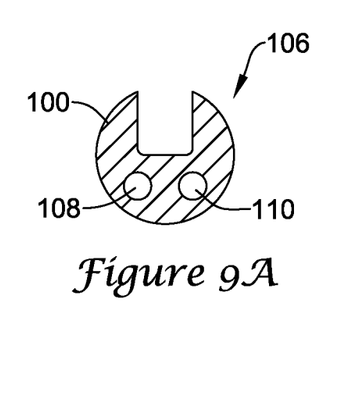
FIGS. 9A-9C are section views along lines 9A-9A, 9B-9B, and 9C-9C of FIG. 8A.
Figure 9B:
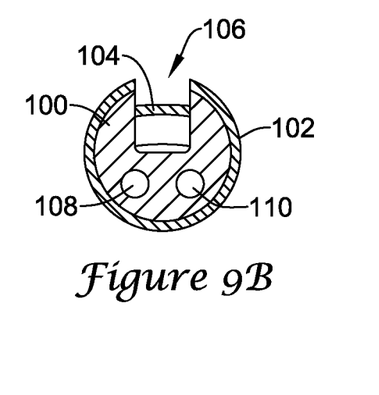
Figure 9C:
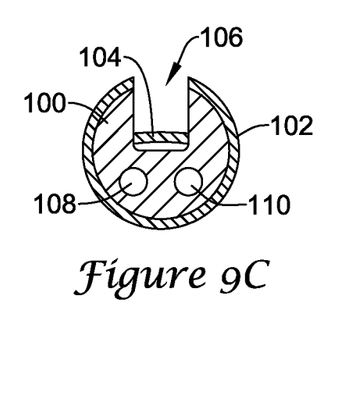

The transverse section views of FIGS. 9A-9C illustrate that the device shaft 100 is shown having the channel 106 as well as auxiliary lumens 108 and 110. As shown in FIG. 9B, along line 9B-9B in FIG. 8A, the flap 104 extends partly into the channel 106, with the optional distal portion of the ramp member 102 extending around the device shaft 100 at that location. FIG. 9C is taken at a more distal location along the device shaft 100 and ramp member 102, as shown by line 9C-9C of FIG. 8A. By this point, the flap 104 extends down to the base of the channel 106. If a guidewire is backloaded into the channel 106, the flap 104 will force the guidewire out of the channel 106. However, if a guidewire is passed distally from a more proximal location, as can be seen in FIG. 8B, the slant of the flap 104 will allow the flap 104 to deflect so that the guidewire may pass with little resistance generated by the flap 104.

Figure 10A:
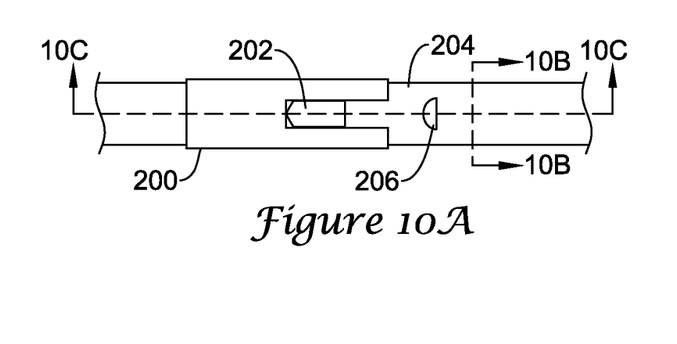
FIGS. 10A-10C, 11A-11C, and 12A-12C illustrate placement of a guidewire exit ramp on another medical device shaft having a closed longitudinally extending laterally accessible guidewire lumen.
Figure 10B:
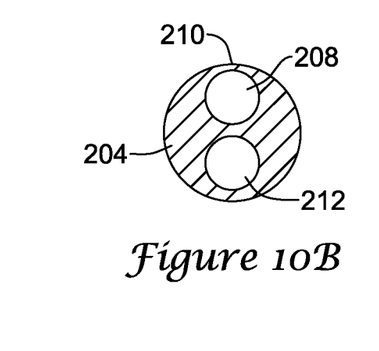
Figure 10C:
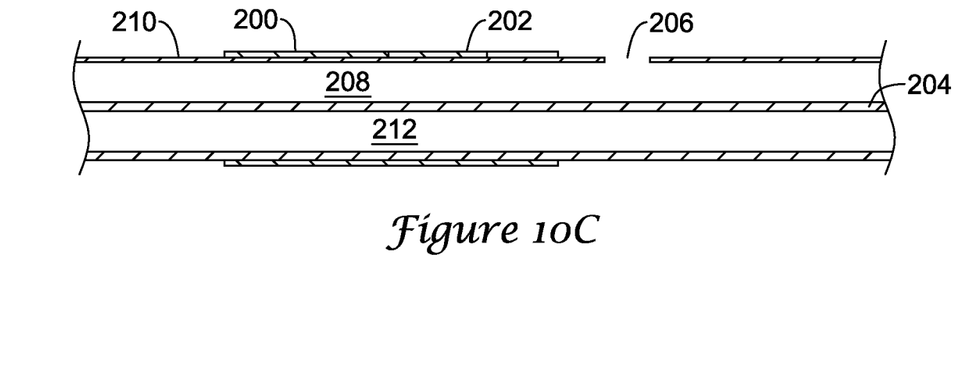

FIGS. 10A-10C, 11A-11C, and 12A-12C illustrate placement of a guidewire exit ramp on another medical device shaft having a closed longitudinally extending laterally accessible guidewire lumen. Referring to FIGS. 10A-10C, a guidewire exit ramp member 200 having a flap 202 is shown placed on a device shaft 204, the device shaft 204 having an opening shown as skive 206. The ramp member 200 may include a proximal end 203 and a distal end 205. The ramp member 200 may further include a slot 201 extending proximally from the distal end 205. The flap 204 may have a proximal end 207 and a distal end 209. The ramp member 200 is shown some distance proximal of the skive 206 on the device shaft 204.

As highlighted in FIG. 10B, (a section view along line 10B-10B of FIG. 10A) the device shaft 204 includes a guidewire lumen 208 having a thinned wall 210, as well as an additional auxiliary lumen 212. The thinned wall 210 enables a guidewire to laterally exit the guidewire lumen 208 by tearing through the thinned wall 210. To further weaken the wall, perforations may be provided. The thinned wall 210 may be provided during extrusion or by post-extrusion machining. The longitudinal cross section of FIG. 10C illustrates the skive opening into the guidewire lumen 208.

Figure 11A:
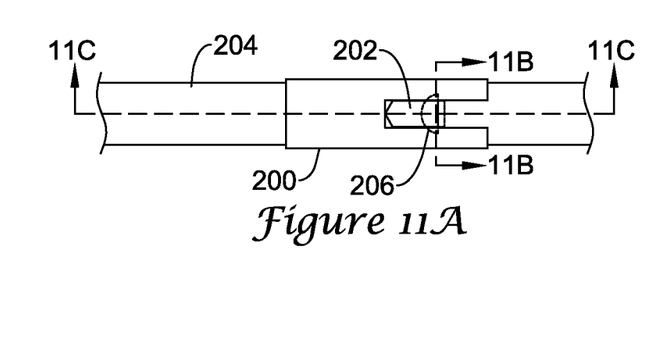
Figure 11B:
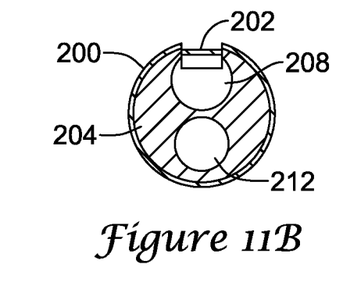
Figure 11C:
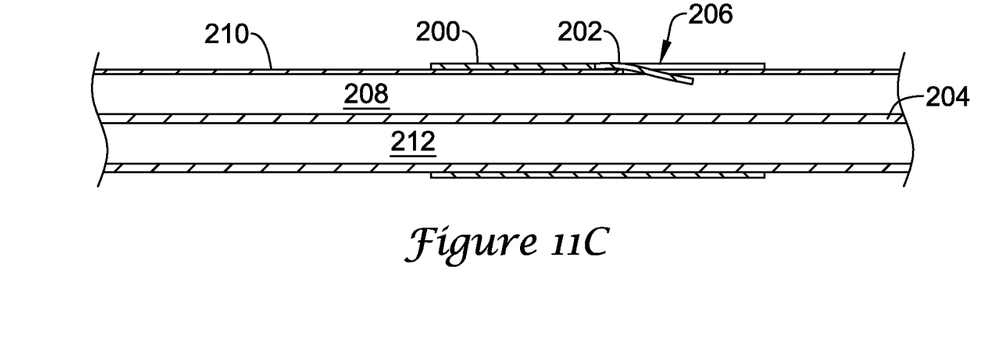

Turning to FIGS. 11A-11C, FIG. 11A shows that the ramp member 200 has been advanced such that the flap 202 partly enters the skive 206 in the device shaft 204 such that the distal end 209 is disposed within the guidewire lumen 206. FIG. 11B shows in transverse cross section that the flap 202 reaches partly down into the guidewire lumen 208 through the skive 206. As shown by FIG. 11C, the skive 206 enables easy entry of the flap 202 down into the guidewire lumen 208 through the thin wall 210. In some embodiments, the flap 202 may be biased downward such that it readily extends through the skive 206. It should be noted that the thinned wall 210 would not be necessary to use the guidewire ramp member 200 in the fashion shown, since the flap 202 simply enters through an opening into the guidewire lumen 208.

Figure 12A:
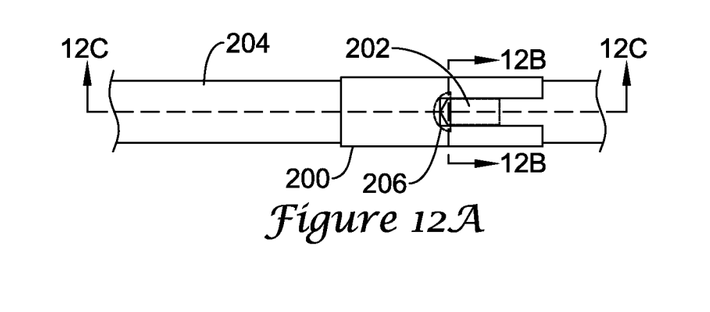
Figure 12B:
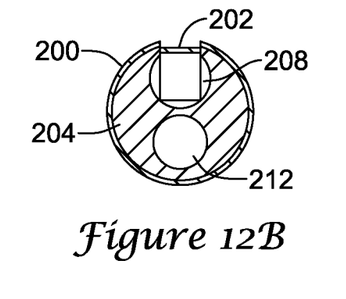
Figure 12C:
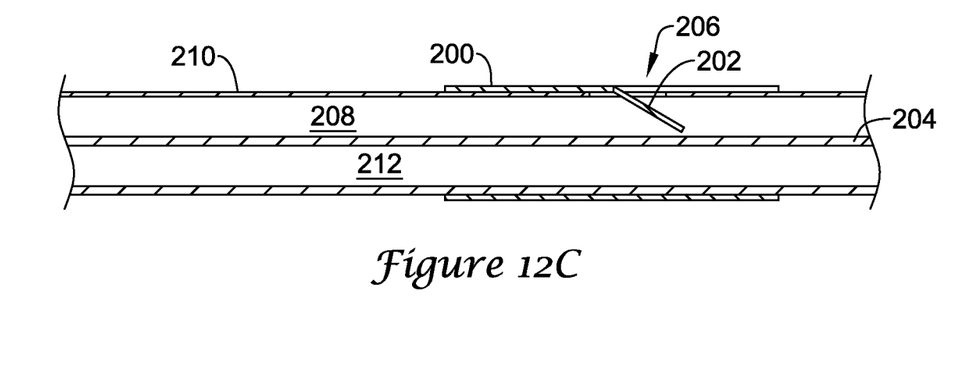

Referring now to FIGS. 12A-12C, the ramp member 200 is moved distally along the device shaft 204 until the flap 202 completely enters the guidewire lumen 208 through the skive 206. Once this location is reached, the flap 202 may rest against an interior wall of the guidewire lumen 208. When so located, a guidewire proximal end passing in a proximal direction through the guidewire lumen 208 may be forced laterally out of the device shaft 204 by the flap 202. Thus backloading of a guidewire into the device shaft 204 can be performed easily with an assurance that a guidewire will exit the device shaft 204 at a desired location defined by the skive 206 and the ramp member 200. In various illustrative embodiments, the ramp member 200 may be moveable with respect to the shaft or secured (by adhesive or welding, for example) to the device shaft 204 once placed as shown in FIG. 12A.

Figure 13A:
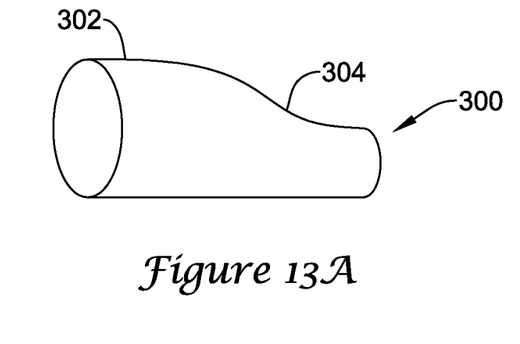
FIGS. 13A-13C illustrate in elevation and section views an alternative embodiment using a relatively stiff plastic guidewire exit ramp member.
Figure 13B:
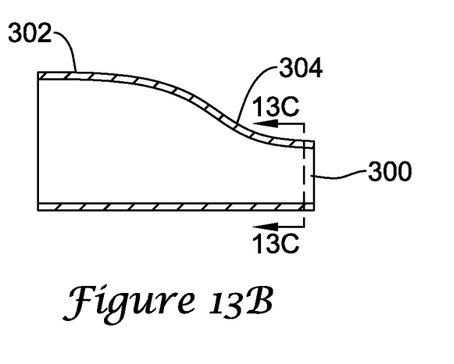
Figure 13C:
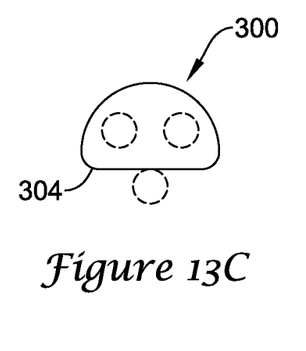

FIGS. 13A-13C illustrate in elevation and section views of an alternative embodiment making use of a pinch or squeeze type of ramp. As can be seen, the ramp member 300 includes a proximal portion 302 and a pinching portion 304. The pinching portion 304 may be sized to reduce the internal diameter or cross-sectional area of the ramp member sufficient to collapse a portion of a guidewire lumen. In one embodiment, the reduced diameter/area is sized to prevent pinching of any auxiliary lumens of an associated medical device, though some compression may be acceptable. It should be noted that the pinching portion need not be cylindrical and may take on a variety of shapes adapted for use with various catheter shafts. As shown in FIG. 13C, the transverse section of the pinching portion 304 is shaped to receive a catheter shaft without pinching any auxiliary lumens, instead being shaped to compress only the guidewire lumen. The dashed lines of FIG. 13C represent, in phantom, the locations of a guidewire lumen and two auxiliary lumens for a catheter shaft received and pinched by the ramp member 300. It can be seen that two of the lumens (the auxiliary lumens) would not be significantly blocked.

Figure 14A:
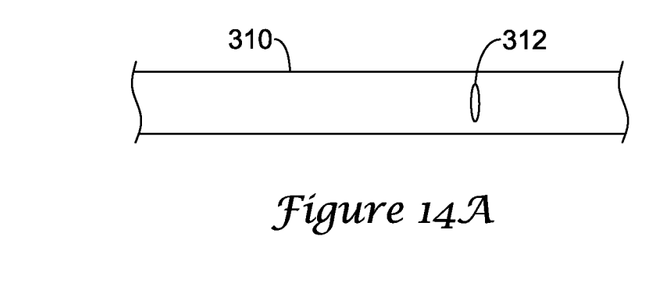
FIGS. 14A-14C illustrate placement of the embodiment of FIGS. 13A-13B on an elongate medical device shaft.
Figure 14B:
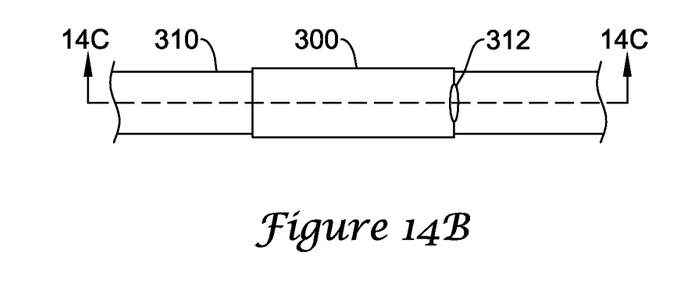
Figure 14C:
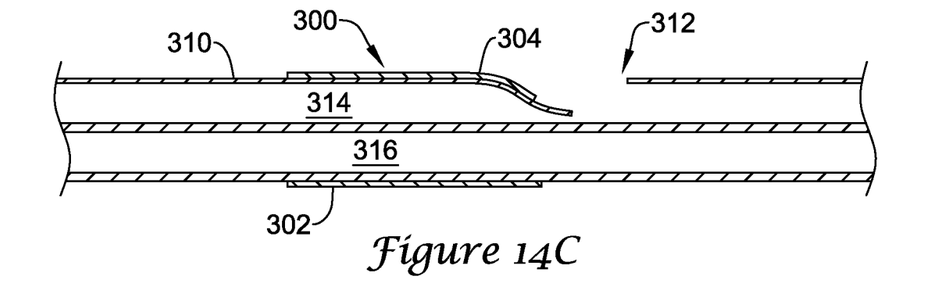

FIGS. 14A-14C illustrate placement of the embodiment of FIGS. 13A-13B on an elongate medical device shaft. As shown in FIG. 14A, the elongate medical device shaft 310 is provided with a transverse cut 312 that may take the form of a skive or slit. If desired, the shaft 310 may include a guidewire lumen having a thinned or weakened wall. As shown in FIG. 14B, the ramp member 300 is slid onto the shaft 310 until the ramp member 300 engages the transverse cut 312. At the location of the transverse cut 312, the shaft 310 will be inherently weaker due to the transverse cut 312 across a portion of the wall of the guidewire lumen. Turning to FIG. 14C, it can be seen that the ramp 304 of the ramp member 300 collapses a portion of the wall of the guidewire lumen 314, but the auxiliary lumen 316 is not significantly affected. The proximal portion 302 aids in letting the ramp 306 collapse the wall of the guidewire lumen 314. A guidewire backloaded into the shaft 310 will now be forced out of the guidewire lumen 314 at the ramp 304. Any suitable plastics may be used for the shaft 310 and the ramp member 300. For the alternative embodiments of FIGS. 13A-13B and 14A-14C, the ramp member 300 may be formed of a stiffer material than the material used to define the guidewire lumen 314. To preserve the patency of the auxiliary lumen 316, some embodiments may make use of a reinforcing member to support the auxiliary lumen 316.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An elongate medical device, comprising:
a substantially elongate shaft having a proximal end, a distal end, and a guidewire lumen extending from the proximal end to the distal end, the guidewire lumen accessible through an opening in the elongate shaft; and
a ramp member disposed over the elongate shaft, the ramp member including a generally tubular proximal portion extending distally from a proximal end of the ramp member, a generally tubular distal portion extending distally from the proximal portion, and a flap extending distally from the proximal portion into the guidewire lumen through the opening.

2. The elongate medical device of claim 1, wherein the guidewire lumen is laterally accessible along a length thereof.

3. The elongate medical device of claim 1, wherein the opening comprises a transverse slit.

4. The elongate medical device of claim 1, wherein the guidewire lumen comprises a thinned wall.

5. The elongate medical device of claim 1, wherein the guidewire lumen comprises a perforation extending from the proximal end to the distal end.

6. The elongate medical device of claim 1, wherein the opening has a first width and wherein the flap has a second width no wider than the first width.

7. The elongate medical device of claim 1, wherein the distal portion of the ramp member comprises a slot extending from a distal end of the proximal portion to a distal end of the distal portion.

8. The elongate medical device of claim 7, wherein the flap at least partially corresponds with the slot in the distal portion.

9. The elongate medical device of claim 1, wherein the flap is biased to extend into the guidewire lumen.

10. The elongate medical device of claim 1, wherein the flap includes a distal end shaped to correspond to a portion of the guidewire lumen.

11. The elongate medical device of claim 1, wherein the flap is flexible such that, when the flap is disposed within the guidewire lumen, a guidewire passing from a location proximal of the flap within the guidewire lumen is readily allowed past the flap in the guidewire lumen.

12. The elongate medical device of claim 1, wherein the flap is shaped such that a guidewire backloaded into the guidewire lumen will be forced out of the guidewire lumen by the flap.

13. The elongate medical device of claim 1, wherein the elongate shaft further includes an auxiliary lumen in addition to the guidewire lumen.

14. An elongate medical device, comprising:
an elongate shaft having a proximal end, a distal end, and a guidewire lumen extending from the proximal end to the distal end, the guidewire lumen accessible through a transverse slit in the elongate shaft; and
a ramp member disposed over and contacting the elongate shaft, the ramp member including a proximal portion, a generally tubular distal portion extending distally from the proximal portion, and an inclined surface extending distally from the proximal portion and extending from an outer surface of the elongate shaft through the transverse slit and into the guidewire lumen such that a guidewire backloaded into the guidewire lumen will be forced out of the guidewire lumen through the transverse slit by the inclined surface.

15. The elongate medical device of claim 14, wherein the inclined surface is biased to extend into the guidewire lumen.

16. The elongate medical device of claim 14, wherein the guidewire lumen is laterally accessible along a length thereof.

17. The elongate medical device of claim 14, wherein the inclined surface is flexible such that, when the inclined surface is disposed within the guidewire lumen, a guidewire passing from a location proximal of the inclined surface within the guidewire lumen is readily allowed past the inclined surface in the guidewire lumen.

18. The elongate medical device of claim 14, wherein the elongate shaft further includes an auxiliary lumen in addition to the guidewire lumen.

19. An elongate medical device, comprising:
an elongate shaft having a proximal end, a distal end, and a laterally accessible guidewire lumen extending from the proximal end to the distal end, the guidewire lumen accessible through an opening in the elongate shaft; and
a ramp member disposed over and contacting the elongate shaft, the ramp member including a proximal portion, a generally tubular distal portion extending distally from the proximal portion, and a flap extending distally from the proximal portion and extending from an outer surface of the elongate shaft through the opening and into the guidewire lumen such that a guidewire backloaded into the guidewire lumen will be forced out of the guidewire lumen through the opening by the flap;
wherein the flap is flexible such that, when the inclined surface is disposed within the guidewire lumen, a guidewire passing from a location proximal of the flap within the guidewire lumen is readily allowed past the flap in the guidewire lumen.

* * * * *